US012640265B2

(12) United States Patent
Hammond

(10) Patent No.: US 12,640,265 B2
(45) Date of Patent: May 26, 2026

(54) AUTOMATED CALIBRATION METHOD AND SYSTEM FOR A DIAGNOSTIC ANALYZER

(71) Applicant: IDEXX Laboratories, Inc., Westbrook, ME (US)

(72) Inventor: Jeremy Hammond, Standish, ME (US)

(73) Assignee: IDEXX LABORATORIES, INC., Westbrook, ME (US)

( * ) Notice: Subject to any disclaimer, the term of this patent is extended or adjusted under 35 U.S.C. 154(b) by 247 days.

(21) Appl. No.: 18/521,307

(22) Filed: Nov. 28, 2023

(65) Prior Publication Data

US 2024/0177849 A1 May 30, 2024

Related U.S. Application Data

(60) Provisional application No. 63/428,535, filed on Nov. 29, 2022.

(51) Int. Cl.
A61B 5/00 (2006.01)
G16H 40/60 (2018.01)
G16H 50/20 (2018.01)
(52) U.S. Cl.
CPC ............. G16H 40/60 (2018.01); G16H 50/20 (2018.01)
(58) Field of Classification Search
CPC ............................ A61B 5/0022; A61B 5/0093
See application file for complete search history.

(56) References Cited

U.S. PATENT DOCUMENTS 8,645,306 B2    2/2014   Hammond

OTHER PUBLICATIONS

Bull et al. "A Study of Various Estimators for the Derivation of Quality Control Procedures from Patient Erythrocyte Indices." American Journal of Clinical Pathology. 1974: 473-481. vol. 61.
Haykin. "Neural Networks: A Comprehensive Foundation. (2nd Edition)" 1998.
Yen et al. "Fuzzy Logic: Intelligence, Control, and Information. Chapter 2" 1998.

*Primary Examiner* — Michael J D'Abreu
(74) *Attorney, Agent, or Firm* — ROSSI, KIMMS & McDOWELL LLP

(57) ABSTRACT

The present disclosure pertains to methods and systems that calibrate a diagnostic analyzer by first determining whether first diagnostic results exceed a predetermined threshold from a first diagnostic target and adjusting one or more laser settings for the diagnostic analyzer in response. New patient samples are interrogated by the diagnostic analyzer, using the adjusted laser parameters, to determine weighted averaged diagnostic results. In a case where the weighted averaged diagnostic results fall outside of the permissible range, multiplying factors for calibration factors that permit the weighted averaged diagnostic results to fall within the permissible range are determined, and the diagnostic analyzer is calibrated by adjusting the calibration factors corresponding to the parameters of the diagnostic analyzer based at least in part on the multiplying factors.

19 Claims, 5 Drawing Sheets

400

100

130 — MEMORY DEVICE SYSTEM

110 — DATA PROCESSING DEVICE SYSTEM

120 — INPUT-OUTPUT DEVICE SYSTEM

AUTOMATED CALIBRATION METHOD AND SYSTEM FOR A DIAGNOSTIC ANALYZER

CROSS REFERENCE TO RELATED APPLICATIONS

This application claims the priority benefit of U.S. Provisional Application No. 63/428,535, filed Nov. 29, 2022, the entire disclosure of which is hereby incorporated herein in its entirety by reference.

TECHNICAL FIELD

Aspects of the present disclosure generally relate to diagnostic instruments for human and veterinary applications, and more specifically relates to methods and systems for calibrating such instruments.

BACKGROUND

Diagnostic instruments have been used for decades in both the human and veterinary markets. These instruments include hematology analyzers, blood chemistry analyzers and other instruments that determine certain physiological properties of patients. In the veterinary market, the VetAutoread™ automated hematology analyzer has been available since at least the 1990's. Some analyzers, like the VetAutoread™ hematology analyzer from IDEXX Laboratories, Inc. of Westbrook, Me., (see, www.idexx.com), utilize a fixed optical reference to determine instrument performance. Other analyzers, like the IDEXX LaserCyte® hematology analyzer, incorporate polymers, referred to as Qualibeads™, with fixed size and index of refraction to ensure optical performance. In addition, some analyzers, like the Sysmex XT-V manufactured by Sysmex Corp. of Hyogo, Japan (see, www.sysmex.com), utilize a fixed cell control material to ensure assay performance based on guidelines provided by organizations like the College of American Pathologists (CAP, Northfield, Ill.; www.cap.org) and the American Society for Veterinary Clinical Pathology (ASVCP).

Flow cytometry is a technique used in hematology (the study of blood) to classify cells in accordance with their size and complexity, by analyzing the characteristics of cells or particles. During the process, a sample of cells or particles is suspended in fluid and injected into the hematology (diagnostic) analyzer. The analyzer uses laser modules to illuminate a sample (cell medium), emitting light in the visible region (380-700 nm) of the wavelength spectrum. The cell medium in the sample passes through the laser at a location dubbed the "integration point." From here, light is scattered based on the refractive properties of anything within the cytoplasm of the cell medium or the surface shape and size of the cell. Detectors read the light scatter emitted from the integration point. The two modes of light analyzed are forward scatter (FSL) and side scatter (SSL). Forward scatter light is proportional to cell size; the bigger the cell, the more light is scattered, the higher the detected signal. The scattered light is converted into a voltage pulse, which embodies an analog signal that can be read. Once these readings have been taken, the analog signal is converted to a digital one through an analog-to-digital conversion (ADC) unit, and the final digital readout can then be stored or displayed on a monitor. The resulting readout takes the form of a scatter plot, with cell count on the y-axis and forward scatter signal on the x-axis. The forward scatter light signal provides a measurement of the mean corpuscular volume (MCV) of a cell. Calibration of the laser parameters (laser tuning) involves determining the optical and digital gains for each laser for both forward scatter and side scatter from cells in a sample. A control signal (extinction or EXT signal) defines light scatter in the absence of any cells in the sample stream.

Human cells are generally utilized in the formulation of fixed-cell controls. These samples may require a specific (human) algorithm that can be very different from veterinary sample algorithms. Fundamentally, the control runs may be stable and accurate, but specific species responses may deviate due to chemical, fluidic, algorithmic, or other reasons. Patient-based methods provide species-specific analyses that can augment performance checks with fixed-cell controls and confirm that the system is performing accurately for each species between scheduled control runs.

The veterinary market is very cost sensitive and control runs, which are expensive, are not run in the same frequency as in human practices, which generally run fixed cell controls approximately at least once per 8-hour shift. Therefore, the use of weighted moving averages performed on patient samples is beneficial to ensuring continued calibration of diagnostic analyzers for veterinary applications. In addition, use of weighted moving averages for calibration adjustment has the additional benefit in veterinary applications that expenses for calibration runs are covered during normal patient runs and do not require extra control materials or consumable usage. Even in diagnostic analyzers with fixed cell controls, the benefit from applying a moving averages algorithm to patient samples can be great, since fixed cell control material analysis loses power with increasing number of patient runs and time between control runs.

Weighted moving averages algorithms have been used since about 1974 for analysis of human diagnostic analyzer performance, starting with Bull's moving averages, sometimes referred to as X-B or $X_B$ (see, Bull B. S., et al., "A study of various estimators for the derivation of quality control procedures from patient erythrocyte indices", Am. J. Clin. Pathol. 1974; Vol. 61:473-481). In automated diagnostic analyzers for human samples, fixed cell controls are commonly used to determine instrument performance and calibration settings. Weighted averages provide the benefit that the analysis is performed on patient samples run on the analyzer and fill the gap between control runs, which are usually once per shift, approximately every eight hours or more frequently as recommended by organizations such as the Clinical and Laboratory Standards Institute (CLSI, Wayne, Pa.; http://www.clsi.org/; 1-877-447-1888). The use of weighted averages can provide an early warning that results may be in question even before the time to run the next control.

Bull's moving averages algorithm, described in detail in U.S. Pat. No. 8,645,306, has been used to track patient results and adjust calibration factors in automated diagnostic analyzers for veterinary applications. There are many benefits of utilizing Bull batches to summarize patient samples into a control chart, which is displayed on the analyzer so that the clinician may determine if the analyzer needs to be re-calibrated, even during the period between fixed cell control tests. The Bull weighted moving averages algorithm provides a means to reduce the impact of single sample variations on batch results. Also, utilizing the analysis for red cell indices, that is, RBC (red blood cells), MCV (mean corpuscular volume), HGB (hemoglobin), HCT (hematocrit), MCH (mean corpuscular hemoglobin), and MCHC (mean corpuscular hemoglobin concentration), has additional benefit since several of the parameters (MCV, MCH, and MCHC) have tight normal variations, within species, that can provide additional information with respect to result accuracy. Many concerns related to specialty practices running multiple sick patients and oncology patients can be mitigated since there are few clinical conditions that drive significant variation in MCV, MCH, and MCHC for a population of patients.

As discussed in U.S. Pat. No. 8,645,306, by removing runs that have clinical flags or impossible responses (such as a zero occurring from a short sample), batch results provide easily charted results that are not heavily weighted by outlier results. More specifically, results are qualified prior to inclusion in the batch analysis. Repeat runs on a particular patient within a batch are removed. Runs that have clinical or analyzer flags are removed. Runs with impossible responses, such as those stemming from a gross instrument error like a short sample, are removed. Batch results provide easily charted values that are not heavily weighted by outlier results due to patient response, sample handling, or analyzer variation. Outlier runs, defined as patient results that report significantly different than the normally measured population on that analyzer either due to patient response or system malfunction, have no significant impact on batches. Due to flagging and other internal checks, these results are often not reported to the user.

Control chart rules are in place in many conventional diagnostic analyzers to provide feedback when the Bull batches show a trend or bias outside of limits. Rules implemented on Bull batches can have higher power than the same number of patient results, since each Bull batch corresponds to a pre-determined number of patient runs. The act of grouping runs into batches that also include prior batch values provides a smoothing effect, so a rule that may otherwise require more points (samples) to be outside the controls can now be utilized with far fewer points being out of control.

U.S. Pat. No. 8,645,306 describes an automated system and method that monitors the performance of diagnostic analyzers based on patient samples and, through feedback based on control chart rules, adjusts the calibration parameters of the analyzer in real time to maintain the analyzer within its calibration specifications. However, the system and method described in U.S. Pat. No. 8,645,306 has two major drawbacks. First, the method described in U.S. Pat. No. 8,645,306 relies on patient samples to determine whether the analyzer is off calibration between control runs. As the health status and size of cells in patient samples varies greatly, a large number (statistically significant) of patient samples is required to determine whether the lasers in the hematology analyzer are off calibration or whether the variation in detected measurements is a result of sample variation. Second, blood samples from different animal species have different size and physical properties. The method of U.S. Pat. No. 8,645,306 is species-specific and requires a large (statistically significant) number of patient samples from each species to properly maintain and adjust the calibration factors for each species.

SUMMARY

At least the above-discussed needs are addressed, and technical solutions are achieved in the art, by various aspects of the present disclosure. Some aspects of the present disclosure pertain to a processor-implemented method of calibrating a diagnostic analyzer having one or more parameters comprising receiving first diagnostic results from the diagnostic analyzer; determining whether the first diagnostic results exceed a predetermined threshold from a first diagnostic target; adjusting, in a case where the first diagnostic results exceed the predetermined threshold, one or more laser settings for the diagnostic analyzer; receiving a plurality of patient samples for interrogation by the diagnostic analyzer; determining weighted averaged diagnostic results associated with the plurality of patient samples interrogated by the diagnostic analyzer using the adjusted one or more laser settings and one or more calibration factors corresponding to the one or more parameters for the diagnostic analyzer; and determining whether the weighted averaged diagnostic results fall outside of a permissible range. In a case where the weighted averaged diagnostic results fall outside of the permissible range, the method further includes determining one or more multiplying factors for the one or more calibration factors that permit the weighted averaged diagnostic results to fall within the permissible range, and calibrating the diagnostic analyzer by adjusting the one or more calibration factors corresponding to the one or more parameters of the diagnostic analyzer based at least in part on the one or more multiplying factors.

In some aspects of the disclosure, the first diagnostic results are obtained by interrogating polymer beads, suspended in a fluidic dye, using the diagnostic analyzer. In some aspects of the disclosure, the first diagnostic results are associated with a control run through the diagnostic analyzer.

In some aspects of the disclosure, the plurality of patient samples originate from a plurality of different species, and the method further includes normalizing the plurality of patient samples to account for cross-species differences.

In some aspects of the disclosure, the permissible range is defined by control chart rules limits.

In some aspects of the disclosure, the one or more laser settings include a red laser forward scatter light (FSL) digital gain and a red laser extinction (EXT) digital gain.

In some aspects of the disclosure, the determining of the weighted averaged diagnostic results further includes assembling the plurality of patient samples into a plurality of batch runs, each batch run containing an equal number of patient samples; determining the weighted average for a first batch run of the plurality of batch runs; calculating an absolute difference between each patient sample in a second batch run of the plurality of batch runs and the average for the first batch run; updating the weighted average for the first batch run using a sum of squared differences of the absolute differences for the second batch run to obtain a new weighted average for the first and second batch runs; and repeating the calculating and updating steps for each subsequent batch run of the plurality of batch runs.

In some aspects of the disclosure, the determining of the one or more multiplying factors further includes setting fuzzy-logic derived confidence intervals for the one or more calibration factors; calculating a variance between a target value and the weighted averaged diagnostic results for the one or more parameters of the diagnostic analyzer; selecting a parameter of the one or more parameters for tuning, incrementally stepping the selected parameter towards the target value, and evaluating other parameters of the one or more parameters after stepping the selected parameter toward the target value; determining whether a stopping criterion is satisfied; and, in a case where the stopping criterion is satisfied, generating the one or more multiplying factors based on the tuned one or more parameters.

In some aspects of the disclosure, in a case where the stopping criterion is not satisfied, the selecting step is repeated to perform further parameter tuning.

In some aspects of the disclosure, the diagnostic analyzer is a hematology analyzer and wherein the one or more parameters include red blood cell count (RBC), mean corpuscular volume (MCV), hemoglobin (HGB), platelet count (PLT), mean platelet volume (MPV), white blood cell count (WBC), hematocrit (HCT), mean corpuscular hemoglobin (MCH), mean corpuscular hemoglobin concentration (MCHC), platelet distribution width (PDW), and red blood cell distribution width (RDW).

Some aspects of the disclosure pertain to a system for calibrating a diagnostic analyzer having one or more parameters, the system including at least one computer accessible-storage device configured to store instructions corresponding to the method aspects discussed above; and at least one processor communicatively connected to the at least one computer accessible storage device and configured to execute the instructions.

Some aspects of the disclosure pertain to a non-transitory computer readable storage medium configured to store a program, executed by a computer, for a system for calibrating a diagnostic analyzer having one or more parameters, the program including instructions corresponding to the method aspects discussed above.

BRIEF DESCRIPTION OF THE DRAWINGS

It is to be understood that the attached drawings are for purposes of illustrating various aspects of the disclosure and may include elements that are not to scale. It is noted that like reference characters in different figures refer to the same objects.

DETAILED DESCRIPTION

Figure 1:
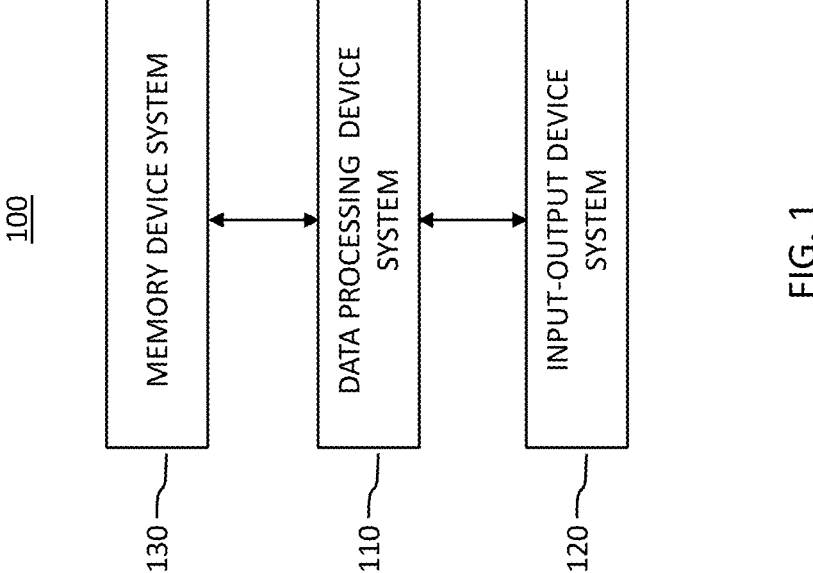
FIG. 1 shows a computing device system, according to some aspects of the disclosure.

In some aspects of the disclosure, the systems described herein execute methods for automated calibration of a diagnostic analyzer using patient sample data. It should be noted that the aspects of the disclosure are not limited to these or any other examples provided herein, which are referred to for purposes of illustration only.

In this regard, in the descriptions herein, certain specific details are set forth in order to provide a thorough understanding of various aspects of the disclosure. However, one skilled in the art will understand that the aspects of the disclosure may be practiced at a more general level without one or more of these details. In other instances, well-known structures have not been shown or described in detail to avoid unnecessarily obscuring descriptions of various aspects of the disclosure.

Any reference throughout this specification to "one aspect," "an aspect," "an example aspect," "an illustrated aspect," "a particular aspect," and the like means that a particular feature, structure or characteristic described in connection with the aspect is included in at least one aspect of the disclosure. Thus, any appearance of the phrase "in one aspect," "in an aspect," "in an example aspect," "in this illustrated aspect," "in this particular aspect," or the like in this specification is not necessarily all referring to one aspect or a same aspect. The phrases embodiment and aspect may be used interchangeably in the disclosure. Thus, any appearance of the phrase "in one aspect," "in an aspect," "in an example aspect," "in this illustrated aspect," "in this particular aspect," or the like in this specification is not necessarily all referring to one aspect or embodiment, or a same aspect or embodiment. Furthermore, the particular features, structures or characteristics of different aspects may be combined in any suitable manner to form one or more other aspects.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects.

In the following description, some aspects of the present disclosure may be implemented at least in part by a data processing device system configured by a software program. Such a program may equivalently be implemented as multiple programs, and some or all of such software program(s) may be equivalently constructed in hardware.

Further, the phrase "at least" is or may be used herein at times merely to emphasize the possibility that other elements may exist beside those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device," the word "machine," the word "system," and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various aspects that a device or machine or device system resides entirely within a same housing to exclude aspects where the respective device, machine, system, or device system resides across different housings. The word "device" may equivalently be referred to as a "device system" in some aspects.

The phrase "derivative thereof" and the like is or may be used herein at times in the context of a derivative of data or information merely to emphasize the possibility that such data or information may be modified or subject to one or more operations. For example, if a device generates first data for display, the process of converting the generated first data into a format capable of being displayed may alter the first data. This altered form of the first data may be considered a derivative of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derivative thereof" or the like is used in reference to the information or data, unless otherwise required by context. As indicated above, usage of the phrase "or a derivative thereof" or the like merely emphasizes the possibility of such changes. Accordingly, the addition of or deletion of the phrase "or a derivative thereof" or the like should have no impact on the interpretation of the respective data or information. For example, the above-discussed color-coded bar chart may be considered a derivative of the respective first data or may be considered the respective first data itself.

The term "program" in this disclosure should be interpreted to include one or more programs including a set of instructions or modules that may be executed by one or more components in a system, such as a controller system or data processing device system, in order to cause the system to perform one or more operations. The set of instructions or modules may be stored by any kind of memory device, such as those described subsequently with respect to the memory device system 130, 251, or both, shown in FIGS. 1 and 2, respectively. In addition, this disclosure may describe or similarly describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). Such descriptions should be deemed to be equivalent to describing that the instructions or modules are configured to cause the performance of the action. The word "module" may be defined as a set of instructions. The word "program" and the word "module" may each be interpreted to include multiple sub-programs or multiple sub-modules, respectively. In this regard, reference to a program or a module may be considered to refer to multiple programs or multiple modules.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms, unless otherwise required or indicated by context. However, non-usage of the phrase "or a derivative thereof" or the like nonetheless includes derivatives or modifications of information or data just as usage of such a phrase does, as such a phrase, when used, is merely used for emphasis.

Further, the phrase "graphical representation" used herein is intended to include a visual representation presented via a display device system and may include computer-generated text, graphics, animations, or one or more combinations thereof, which may include one or more visual representations originally generated, at least in part, by an image-capture device.

Figure 4:
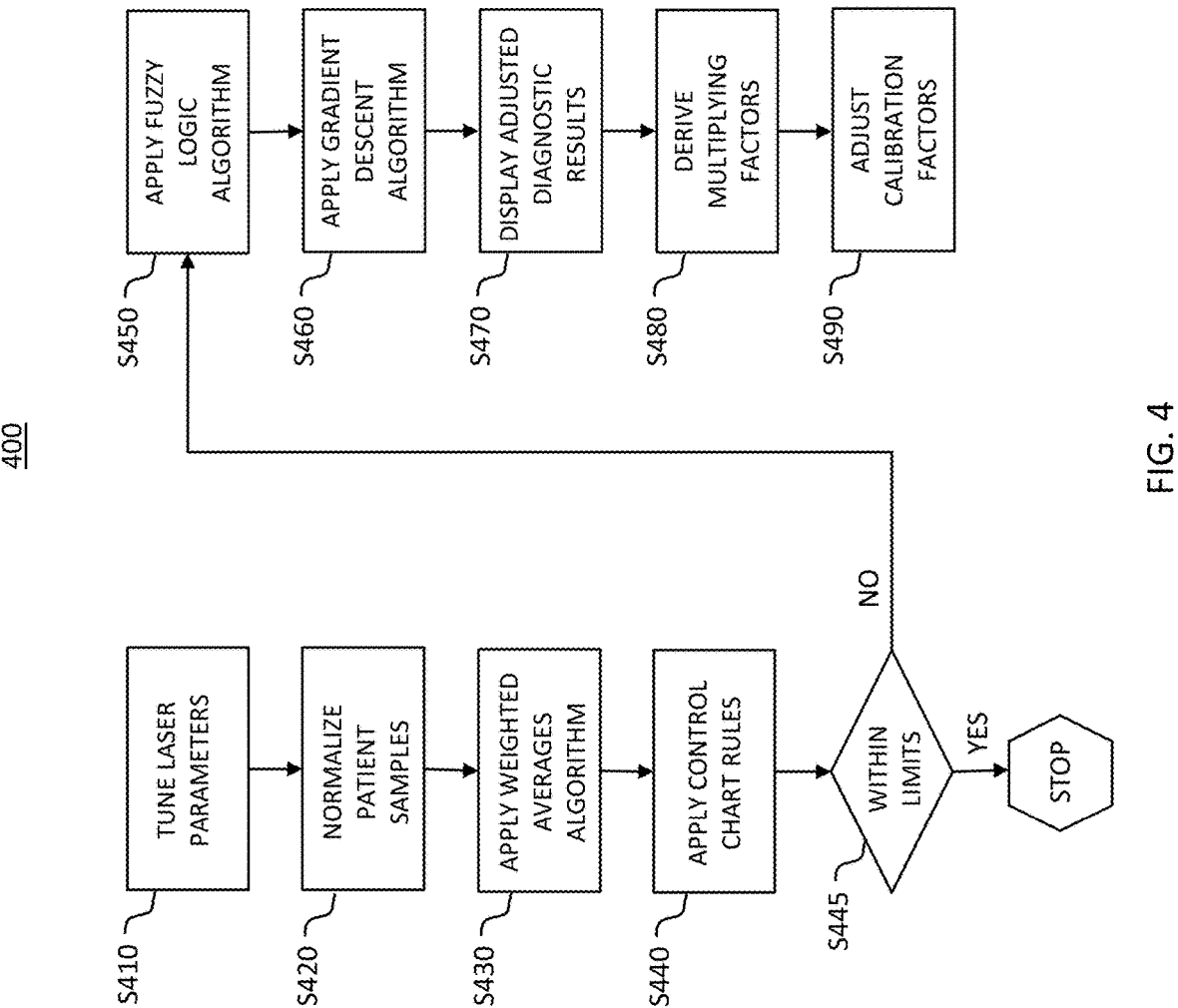
FIG. 4 shows a flowchart of a method of calibrating a diagnostic analyzer, according to some aspects of the disclosure.

Further still, example methods are described herein with respect to FIG. 4. Such figures are described to include blocks associated with computer-executable instructions. It should be noted that the respective instructions associated with any such blocks herein need not be separate instructions and may be combined with other instructions to form a combined instruction set. The same set of instructions may be associated with more than one block. In this regard, the block arrangement shown in method FIG. 4 herein is not limited to an actual structure of any program or set of instructions or required ordering of method tasks, and such method FIG. 4, according to some aspects, merely illustrates the tasks that instructions are configured to perform, for example upon execution by a data processing device system in conjunction with interactions with one or more other devices or device systems.

Figure 2:
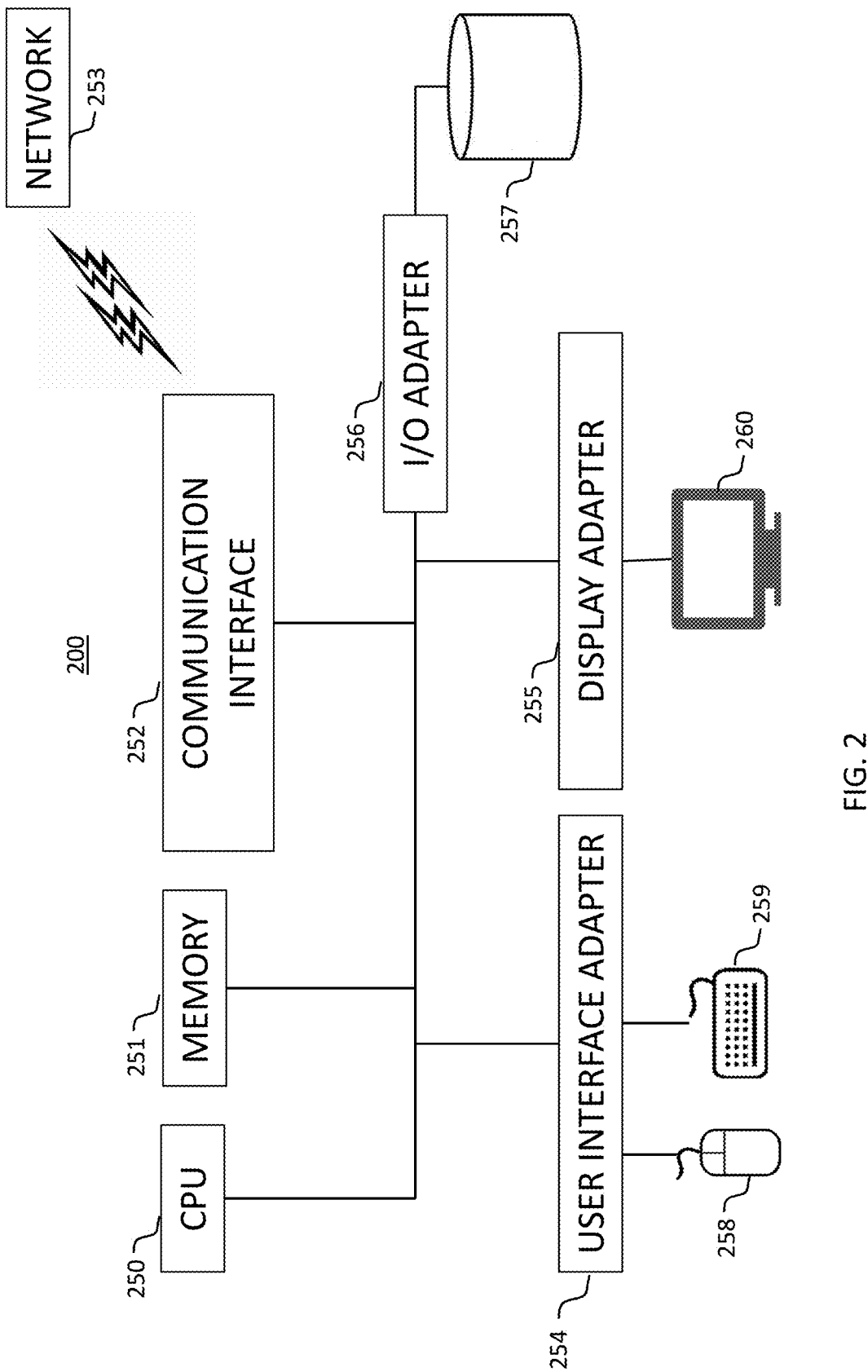
FIG. 2 shows another computing device system, according to some aspects of the disclosure.

FIG. 1 schematically illustrates a system 100 according to some aspects of the disclosure. In some aspects of the disclosure, the system 100 may be a computing device 200 (as shown in FIG. 2). In some aspects, the system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as one or more of those in the system 100, control programs associated with some of the various aspects of the disclosure. Each of the phrases "data processing device," "data processor," "processor," and "computer" is intended to include any data processing device, such as a central processing unit ("CPU"), a desktop computer, a laptop computer, a mainframe computer, a tablet computer, a personal digital assistant, a cellular phone, and any other device configured to process data, manage data, or handle data, whether implemented with electrical, magnetic, optical, biological components, or other.

The memory device system 130 includes one or more processor-accessible memory devices configured to store information, including the information needed to execute the control programs associated with some of the various aspects of the disclosure. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs (Read-Only Memory), RAMs (Random Access Memory), and cloud-based (non-local) storage systems. In some aspects of the disclosure, each of the phrases "processor-accessible memory" and "processor-accessible memory device" is intended to include a non-transitory computer-readable storage medium. In some aspects of the disclosure, the memory device system 130 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some aspects of the disclosure.

The input-output device system 120 may include a mouse, a keyboard, a touch screen, another computer, or any device or combination of devices from which a desired selection, desired information, instructions, or any other data is input to the data processing device system 110. The input-output device system 120 may include any suitable interface for receiving information, instructions or any data from other devices and systems described in various ones of the aspects of the disclosure.

The input-output device system 120 also may include an image generating device system, a display device system, a speaker device system, a processor-accessible memory device system, or any device or combination of devices to which information, instructions, or any other data is output from the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the aspects of the disclosure. In this regard, the input-output device system may include various other devices or systems described in various aspects of the disclosure.

FIG. 2 shows an example of a computing device system 200, according to some aspects of the disclosure. The computing device system 200 may include a processor 250, corresponding to the data processing device system 110 of FIG. 1, in some aspects of the disclosure. The memory 251, input/output (I/O) adapter 256, and non-transitory storage medium 257 may correspond to the memory device system 130 of FIG. 1, according to some aspects of the disclosure. The user interface adapter 254, mouse 258, keyboard 259, display adapter 255, and display 260 may correspond to the input-output device system 120 of FIG. 1, according to some aspects of the disclosure. The computing device 200 may also include a communication interface 252 that connects to a network 253 for communicating with other computing devices 200.

Various methods 400 may be performed by way of associated computer-executable instructions according to some example aspects of the disclosure. In various example aspects of the disclosure, a memory device system (e.g., memory device system 130) is communicatively connected to a data processing device system (e.g., data processing device systems 110, otherwise stated herein as "e.g., 110") and stores a program executable by the data processing device system to cause the data processing device system to execute various aspects methods 400 via interaction with at least, for example, various databases (for example data storage memories 330). In these various aspects of the disclosure, the program may include instructions configured to perform, or cause to be performed, various ones of the instructions associated with execution of various aspects of methods 400. In some aspects of the disclosure, methods 400 may include a subset of the associated blocks or additional blocks than those shown in FIG. 4. In some aspects of the disclosure, methods 400 may include a different sequence indicated between various ones of the associated blocks shown in FIG. 4.

Figure 3:
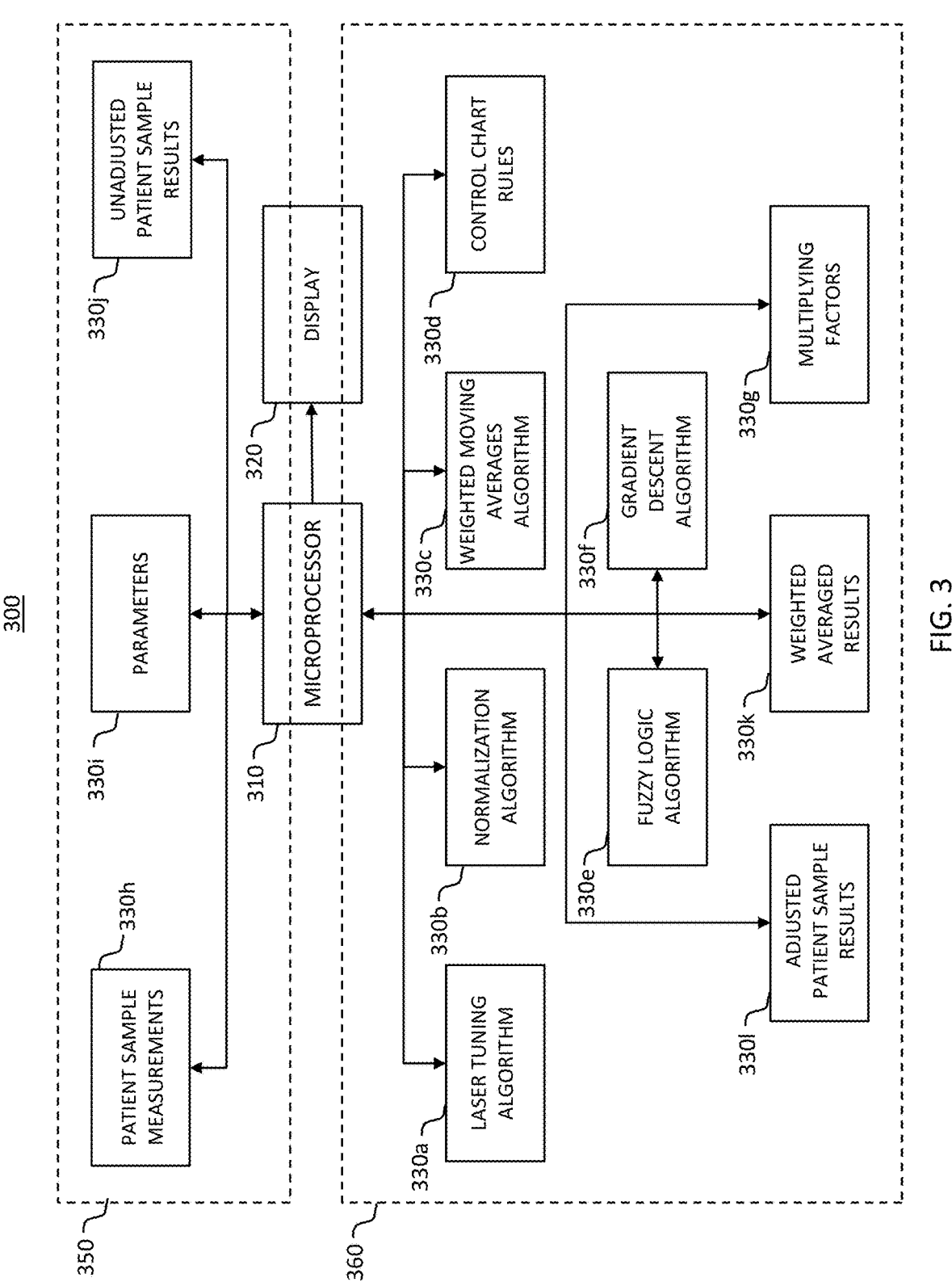
FIG. 3 shows a block diagram of a calibration system, according to some aspects of the disclosure.

According to some aspects of the present disclosure, the system 100, 200 includes some or all of the calibration system 300 shown in FIG. 3, or vice versa. In this regard, FIG. 3 illustrates a system 300, according to some aspects of the present disclosure. The system 300 may be a particular implementation of the system 100, 200, according to some aspects. The system 300 may include a microprocessor 310, a display 320, and one or more memories 330a-3301 that store data and instructions, which generate and operate on the stored data, to adjust one or more calibration factors to calibrate a diagnostic analyzer.

In this regard, FIG. 3 is a block diagram of a calibration system 300 which implements an automated calibration method 400 for a diagnostic analyzer 350 according to various aspects of the present disclosure. In some aspects of the disclosure, the system 300 may be realized by software 360, or an application program, running on a microprocessor 310, or by firmware or hardware implementing the program. The system 300 may include one or more memories 330 (for example, 330a-330l), such as an EEPROM (electronically erasable programmable read only memory), which store various data files and program modules associated with the automated calibration method 400. In some aspects of the disclosure, a memory module 330a stores instructions that implement a laser tuning algorithm, a memory module 330b stores instructions that implement a cross-species normalization algorithm, a memory module 330c stores instructions that implement a weighted moving averages algorithm, a memory module 330*d* stores control chart rules, a memory module 330*e* stores a fuzzy logic algorithm for adjusting the calibration factors, and a memory module 330*f* stores instructions for a gradient descent algorithm.

Memory modules are also provided for storing the multiplying (adjustment to calibration) factors (memory module 330*g*), the patient sample measurements determined by the analyzer (memory module 330*h*), the pre-set calibration factors and laser tuning parameters of the analyzer (memory module 330*i*), the unadjusted diagnostic results of patient samples calculated by the analyzer using the pre-set calibration factors and the laser tuning parameters (e.g., optical gain) of the analyzer (memory module 330*j*), the weighted averaged diagnostic results (memory module 330*k*) resulting from the application of the weighted moving averages algorithm, and the adjusted or corrected diagnostic patient sample results (memory module 330*l*) resulting from the application of the multiplying factors obtained using fuzzy logic and the gradient descent algorithm. In various aspects of the disclosure, the memory modules 330*a*-330*l* may be provided by various combinations of one or more physical memory or storage devices. As a non-limiting example, the program instruction memory modules 330*a*-330*f* may be stored in a first memory as firmware or software application and the data storage memory modules 330*g*-330 may be stored in a second memory in the form of data files or databases.

In some aspects of the disclosure, a microprocessor, microcontroller, or CPU 310 may be employed to carry out the application of the laser tuning algorithm, cross-species normalization algorithm, weighted moving averages algorithm, the control chart rules, the fuzzy logic and the gradient descent algorithm to the patient data, or make any comparisons to determine if the weighted averaged diagnostic results are within the control chart rule limits or ranges, and derive the multiplying factors to be applied to the analyzer's pre-set calibration factors. Of course, it should be realized that such structure (e.g., memories, microprocessor and the like) may already exist within the diagnostic analyzer, and such structure may be conveniently utilized in performing the functions of the automated calibration method of the present disclosure.

FIG. 4 is a high-level flowchart of a method 400 for real time, automated calibration of a diagnostic analyzer, such as a hematology analyzer, according to some aspects of the disclosure. In step S410, polymer beads or particles having a known size and refraction index are run through the diagnostic analyzer to tune laser parameters (for example, the red laser forward scatter light (FSL) digital gain). In step S420, cross-species patient data obtained by running patient samples through the diagnostic analyzer using the pre-set calibration factors, after tuning of the laser parameters using the polymer beads, is normalized and aggregated to increase calibration power and to define an optimal calibration across different species of animals. In step 430, a weighted moving averages algorithm is applied to the normalized unadjusted patient sample diagnostic readings resulting from the analyzer's calculations. In some aspects of the disclosure, the weighted moving averages algorithm is based on Bull's algorithm. The analyzer calculates the unadjusted diagnostic results using the analyzer's pre-set calibration factors and parameters after laser tuning (such as the digital gain for red laser FSL and red laser extinction (EXT), for example). The weighted moving averages algorithm provides weighted averaged diagnostic results.

In step S440, Westgard Rules or any other statistical process control (SPC) chart rules are applied to the weighted averaged diagnostic results. The control chart rules (for example, Westgard Rules) create limits or ranges which are used to test the extent to which the weighted averaged diagnostic results reside within such limits or ranges. Thus, the weighted averaged diagnostic results are compared in step S440 with such control chart rule limits or ranges. If the weighted averaged diagnostic results fall within the control chart rule limits or ranges (NO is step S445), then no multiplying factor needs to be applied to the pre-set calibration factors to adjust the patient sample diagnostic results calculated by the analyzer and the method ends.

However, should the weighted averaged diagnostic results fall outside of the control chart rules limits or ranges (YES in steps S445), then, in steps S450 and S460, fuzzy logic (step S450) and gradient descent algorithms (step S460) are applied to the weighted averaged diagnostic results to obtain adjusted diagnostic results of the patient samples, which are brought within the acceptable limits or ranges of the control chart rules. Such adjusted diagnostic results are stored in memory or read out or displayed by the analyzer in step S470 and represent a more accurate calculation of the patient sample diagnostic results.

In some aspects of the disclosure, in step S480, one or more multiplying factors (for adjusting the calibration factors) are derived from the application of the fuzzy logic (step S450) and the gradient descent algorithm (step S460) to the weighted averaged diagnostic results. In step S490, the multiplying factor (or factors) are used to modify the pre-set calibration factors, so that future patient sample runs utilize the adjusted calibration factors and the adjusted laser tuning parameters. Thus, for example, by applying the derived multiplying factor, the overall gain to the analyzer's optical system may be effectively adjusted from 1.03 to 1.04 to more accurately provide patient sample diagnostic results read out or displayed by the analyzer.

The calibration method is preferably applied each time the diagnostic analyzer generates patient sample results so that the calculated results are automatically adjusted in real time, and the multiplying factor (which is applied to the analyzer's pre-set parameters) continually changes the pre-set calibration factors in real-time, as required, in order to provide more accurate patient readings.

In some aspects of the disclosure, calibration factors are set for at least six parameters of a diagnostic analyzer during instrument manufacturing and servicing (for example, using control runs). These parameters include red blood cell count (RBC), mean corpuscular volume (MCV), hemoglobin (HGB), platelet count (PLT), mean platelet volume (MPV), and white blood cell count (WBC). Three additional parameters, hematocrit (HCT), mean corpuscular hemoglobin (MCH), and mean corpuscular hemoglobin concentration (MCHC) are calculated from the RBC, MCV, and HGB parameters. In some aspects, other parameters such as platelet distribution width (PDW) and red blood cell distribution width (RDW) may be calculated. During field use, the analyzer 350 may drift out of calibration and the calibration factors need to be periodically adjusted, as necessary.

Using standardized particles or polymer beads, such as IDEXXs Qualibeads™ or SmartQC beads, simplifies the algorithm for fine tuning and adjusting the calibration of the lasers in the diagnostic analyzer (step S410 of the calibration method 400). Particles or polymer beads having known size and refraction characteristics eliminate sample variability and permit the adjusting of bias (drift) in analyzer response due to drift in laser tuning parameters. In some aspects of the disclosure, the laser tuning algorithm (step S410) runs a set of polymer beads with known size and physical characteristics through the diagnostic analyzer to measure the particle count and size. These measurements are compared to the known standard responses for the set of polymer beads to determine digital gains to be applied to the measurements to correct for discrepancies. In some aspects of the disclosure, the laser tuning algorithm generates digital gains for forward scatter light (FSL) and no sample (EXT). In some aspects of the disclosure, the FSL digital gain is adjusted when the difference between the measured value and the set parameters is more than a pre-determined threshold, for example 2%.

In some aspects of the disclosure, before the patient samples are normalized to remove species variations, various data filtering operations may be performed to remove runs that may falsely trigger out of control points. For example, in some aspects of the disclosure, patient samples flagged as "SUSPECT", "Not Set", or "Not Calculated", samples from anemic patients, and multiple samples (within a predetermined time period) from the same patient may be removed from the data set.

In some aspects of the disclosure, the cross-species normalization algorithm (step S420) normalizes one or more of RBC, MCV, HGB, PLT, MPV, PDW, RDW, WBC, HCT, MCH, and MCHC for each patient sample run to its species-specific target (result/target). If the result of the run is higher than the target the normalization will be >1, and if the result of the run is lower than target values the normalization will be <1. The values are all normalized to 1.00, so that species no longer plays a role in the calibration. This permits the automated calibration algorithm to leverage a plurality of sparse sets of species-specific samples to generate a statistically significant set of non-species specific sample to determine runs (for example, Bull's batches).

One or more of the FSL and EXT gains are used to adjust the calibration factor for MCV (and MPV) based on the number of patient sample runs. For example, if there are more than 20 runs (Bull's batches), then any difference more than, for example, 2% is adjusted. If there are less than 20 runs but more than 10, then any difference more than, for example, 5%, is adjusted. If there are less than 10 runs, the adjustment factor is calculated and shown to the user, but more runs are recommended before adjusting. For each patient sample, the measured value for MCV and the calculated value for HCT, MCH, and MCHC are recalculated using the adjusted calibration factor for MCV, derived from the FSL digital gain. In some aspects of the disclosure, the MCV calibration factor may also be adjusted to account for reagent or fluidic components in the system.

A weighted moving averages algorithm, such as the Bull's algorithm, is applied in step S430 on the filtered and normalized set of patient data to generate weighted averaged diagnostic patient sample results. Generally, Bull's algorithm groups 20 consecutive patient results into a single Bull batch. However, any predetermined numbers of patient results may be used to assemble Bull batches. The following logic flow describes the steps for generating summary batches from individual patient results using Bull batch values:

1. Determine the average of the first N=20 samples; this is the first Bull batch;
2. For each of the next N=20 samples, calculate the absolute difference between each patient result and the previous Bull batch;

3. Sum all of the values from step (2), maintaining the sign of the difference within the sum;
4. Square the result from Step (3) and divide by N;
5. Add the result from Step (4) to the previous Bull batch to define the current Bull batch; and
6. Repeat Steps (2)-(5) for all remaining Bull batch calculations.

Figure 5:
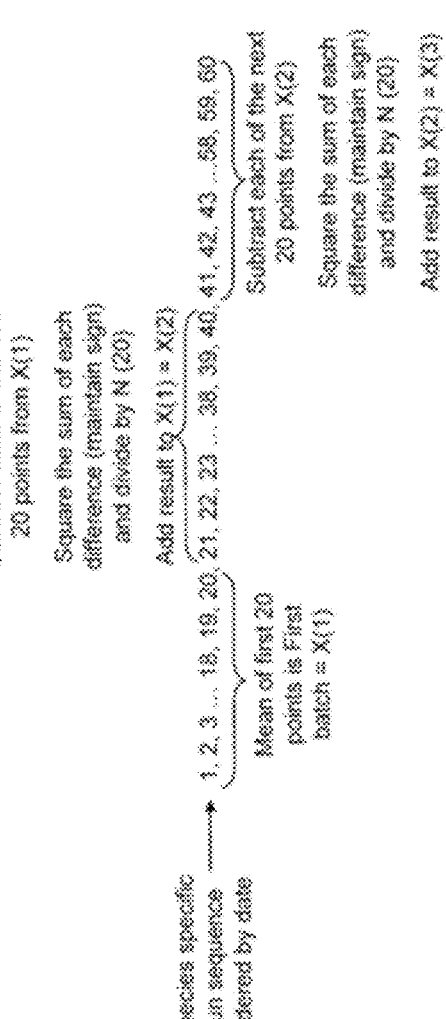
FIG. 5 shows a graphical representation of the Bull's algorithm for generating batch runs, according to some aspects of the disclosure.

A graphical representation/flow chart of the steps described above in applying Bull's algorithm to generate summary batches from individual patient results is shown in FIG. 5.

Control chart rules (such as Westgard Rules) are implemented by the method 400 to provide feedback when the Bull batches show a trend or bias outside of certain limits. For example, two rules may be selected for control charts using Bull batches. The first rule, identified as $2_{SL}$, generates a control error is generated when two consecutive batches exceed the same specified limit. The second rules, identified as $4_X$, generates a control error when four consecutive batches fall on one side of the target. In veterinary applications, in particular, limits have been defined for MCV, MCH, and MCHC based on independent studies of species specific variation. Thus, in some aspects of the disclosure, in step S440, the control chart rules are applied to the recalculated MCV, MCH, and MCHC values in the Bull batches to determine whether they are in control. If the recalculated values are determined to be in control, no further adjustment of the calibration factors is needed (NO in step S445) and the user is notified of the changes to the FSK digital gain and the adjustment to the MCV calibration factor.

If, however, the application of the control chart rules shows that the recalculated MCV, MCH, and MCHC values are outside control limits (YES in step S445), RBC and HGB calibration evaluation will be performed. First, the magnitude of adjustment necessary for RBC and HGB is determined based on the normalized data. In some aspects of the disclosure, the parameter that requires the greatest adjustment (is farthest away from 1.00) is selected and the value needed to get the bias to match the remaining parameter is calculated using fuzzy logic and gradient descent. This adjustment centers the MCH calculation and will adjust MCHC as any bias for RBC and HGB will now be balanced. The adjustments to the RGB or HGB factors are recomputed until the method determines that the MCV, MCH, and MCHC are in control based on the calculated RBC or HGB adjustments.

The relationships between RBC (M/ul), MCV (fl), and HGB (g/dl) to the calculated parameters HCT (%), MCH (g), and MCHC (g/dl) provide the basis for adjustments to the measured parameters. The relationships between HCT, MCH, and MCHC are displayed in Equations 1, 2, and 3, respectively, as shown below:

$$HCT=(RBC*MCV)/10 \tag{Eq. 1}$$

$$MCH=10*(HGB/RBC) \tag{Eq. 2}$$

$$MCHC=1000*HGB/(RBC*MCV) \tag{Eq. 3}$$

Since MCV, MCH, and MCHC have targets and ranges, Equations 1 through 3 provide three equations with three unknowns (RBC, HGB, and HCT). Since MCH and MCHC are not independent equations (MCH is related to MCHC directly by MCV), there are now only two equations (Eqs. 1 and 3) with three unknowns (RBC, HGB, and HCT). In some aspects of the present disclosure, a gradient descent algorithm (see, Haykin, Simon, "Neural Networks: A Comprehensive Foundation" (2nd Edition), 1998) and fuzzy logic (see, Yen, John and Reza Langari, "Fuzzy Logic: Intelligence, Control, and Information", 1998) are employed to provide optimized RBC and HGB adjustments to pair with MCV adjustments (based on the MCV target) for HCT, MCH, and MCHC. A simple confirmation of results can be made by splitting a patient sample and performing a spun HCT (PCV) to confirm results.

More specifically, fuzzy logic algorithms are utilized in step S450, in addition to the system of equations above, to incorporate expert human decisions. Fuzzy logic provides an improvement over traditional logic programming, where case statements (if-then) are used to determine if an expression is true or false, with appropriate actions for either condition. Fuzzy logic assigns levels of correctness; for example, a value can be 30% or 70% true. An example of an application of fuzzy logic is determining if a person's age of 35 is old or young, which depends on the point of origin for the comparison. Fuzzy logic attempts to incorporate expert logic within context. In some aspects of the disclosure, fuzzy logic is incorporated in the calibration method using a software-implemented expert system in the analysis of hematology results and comparison with split references describes each logical input that defines action based on the data. These logical inputs are then translated into fuzzy relationships that the software tool uses moving forward. The logical inputs are essentially training sets for the fuzzy logic algorithm that are then implemented and compared with new test cases.

In some aspects of the present disclosure, fuzzy logic is implemented using targets, ranges, and Equations 1-3, and this combination provides a basis for determining analyzer system adjustments that will positively impact the analyzer's calculated results. A Gaussian or proportional correlation function may be used to describe the "correctness" of a given set of parameter's impact on response to target, based on expert system analysis. Fuzzy logic correlation functions have a maximum peak at the optimal target response and decline as the response moves away from optimal.

The gradient descent algorithm (see, Haykin, Simon, "Neural Networks: A Comprehensive Foundation" (2nd Edition), 1998) (step S460) provides a technique to find minima of a function while only having knowledge of the function in a region close to current position. The general approach is to start at a location (no prior knowledge is needed for starting point, but the algorithm will converge more quickly as one starts closer to the minima) and determine the slope of the function at that location. The slope is used to determine the direction to travel towards the minima and the magnitude of the step. A scalar multiplier can be applied to the slope magnitude to accelerate or temper the size of the step. Small steps will require longer time to converge, while large steps are more likely to move too far and could cause oscillations around the minima.

Gradient descent is used to solve Equations 1-3, since there is no deterministic closed form solution to find the minima. The idea is that MCHC can be increased by increasing HGB, or by decreasing RBC and/or MCV. Evaluation of MCH will provide information unrelated to MCV, while evaluation of HCT will provide information unrelated to HGB. By moving in the right direction on RBC, MCV, and/or HGB, an optimal response can be obtained for all of these calculated relationships. In some aspects of the disclosure, the gradient descent is performed by determining whether stepping the selected parameter closer to the target would have a beneficial effect on MCHC and MCH with respect to their targets. If the selected parameter is RBC, the effect on HCT with respect to its target may be used instead of the MCHC and MCH. However, a fuzzy value is applied to HCT to have lower power than MCH and MCHC. During gradient descent, as the RBC or HGB values are stepped closer to their targets, their effects on MCHC, MCH, and/or HCT are continually evaluated until a stopping criterion is met. In some aspects of the disclosure, the gradient descent is stopped when the MCH and MCHC (or HCT) values are within an acceptable range from the target (for example, 1%, 2%, or 3%).

In some aspects of the disclosure, the fuzzy logic algorithm continues to adjust the RBC and/or HGB values past their targets in order to get the MCH, MCHC, and/or HCT values to fall within their targets. It has been observed that the population for MCH and MCHC is much tighter than RBC and HGB; thus, this fuzzy logic can provide better calibration results.

In some aspects of the disclosure, the gradient descent algorithm adjusts the values of RBC or HGB towards the target in 1% step increments, and calculates the effects of these step increments on MCH, MCHC, and/or HCT. If it is determined that RBC and HGB are oscillating or marching together and not changing MCH and MCHC bias, then the step increment iterations are stopped.

One common pitfall to the gradient descent algorithm can manifest if there are local minima in the function where the algorithm could get stuck and never reach the global minima. The benefit of the system of equations discussed above is that local minima are not present, since the relationships are all first order, and the logic should always converge at the global minima.

The gradient descent approach provides a way to optimize RBC, MCV, and HGB with criteria related to the HCT, MCH, and MCHC responses. Fuzzy logic is used to provide weighting with respect to the differences between responses and species specific targets. The correlation function takes the result of the N Gaussian functions for each parameter (RBC, MCV, HGB, HCT, MCH, MCHC) as a function of Bull batch. The outcome is a single value that defines how correlated the results are based on the adjustments. Optimizing this correlation function output value provides the basis for the gradient descent minimizing algorithm. In some aspects of the disclosure, a 2-d gradient descent algorithm can be used to optimize RBC and HGB with respect to HCT, MCH, and MCHC, since MCV already has a target value from the FSL digital gain.

It should be noted, however, that the calibration systems and methods described above are not limited to optimizing RBC, MCV, and HGB with criteria related to the HCT, MCH, and MCHC responses, but can be used to optimize other parameters as well.

For example, in some aspects of the disclosure, the system 300 and method 400 is used to optimize the mean platelet volume (MPV), red blood cell distribution width (RDW), and platelet distribution width (PDW). PDW is a measure of the variation in the size of platelets. It is expressed as a percentage and is calculated by dividing the standard deviation of platelet volume by the mean platelet volume (MPV). A normal PDW is between 10% and 20%. An abnormally high PDW may be indicative of conditions such as liver disease, inflammation, or myeloproliferative disorders. An abnormally low PDW may be associated with conditions such as iron deficiency anemia, vitamin B12 deficiency, or idiopathic thrombocytopenia purpura (ITP). RDW is a measure of the variation in the size of red blood cells. It is expressed as a percentage and is calculated by dividing the standard deviation of red blood cell volume by the mean red blood cell volume (MCV). A normal RDW is between 11.5% and 14.5%. An abnormally high RDW may be indicative of conditions such as anemia, iron deficiency, or vitamin B12 deficiency. An abnormally low RDW may be associated with conditions such as thalassemia or sickle cell anemia. Both PDW and RDW are non-specific parameters, meaning that they can be elevated or decreased in a variety of conditions. However, they can be helpful in providing clues to the underlying cause of a patient's hematological abnormalities.

MPV and PDW are both a function of EXT (the no sample control/extinction signal). Thus, in some aspects of the disclosure, the MPV and PDW calibration is adjusted using fuzzy logic and gradient descent whenever the EXT is adjusted. The general steps for adjusting these parameters include determining whether the hematology analyzer is calibrated properly based on the EXT precision and ExT baseline values. If the calibration is outside the acceptable range, the EXT adjustment (red laser gain adjustments) are calculated. The EXT digital gain can be computed by running a control run of polymer beads through the analyzer. Next, it is determined whether the EXT adjustment would move the MPV and PDW outside the acceptable range. If yes, then MPV and PDW calibration factors need to be adjusted.

In some aspects of the disclosure, the MPV parameter is a function of the red laser EXT peak mean for the platelet population with EXT digital gain applied. As with RBC and HGB calibration adjustment, the runs (patient samples) are filtered to remove samples where the platelet values are below a certain threshold, so that outliers do not overinfluence the calibration process. Further, runs with qualified platelet values ("SUSPECT", "NOT SET", etc.) are also removed. The MPV calibration factor and the previous red EXT gain is unapplied from the runs and the adjusted red EXT digital gain, from the previous step, is applied instead. For all runs, the updated MPV is calculated based on the current calibration factor and percentage of runs that are above or below the species-specific reference interval are determined. Next, fuzzy logic and gradient descent is used to calculate the smallest MPV calibration factor change that results in minimum reported values outside normal reference intervals. Note that the smallest MPV calibration factor change may be no change if there is no way to reduce the percentage of runs outside the reference interval.

PDW is similar to MPV but is only calculated for canine samples. Similar to MPV, the runs are filtered to remove outliers and qualified values. The PDW calibration factor and the previous red EXT gain is unapplied from the runs and the adjusted red EXT digital gain, from the previous step, is applied instead. For all runs, the updated PDW is calculated based on the current calibration factor and percentage of runs that are above or below the species-specific reference interval are determined. Next, fuzzy logic and gradient descent is used to calculate the smallest PDW calibration factor change that results in minimum reported values outside normal reference intervals.

Unlike MPV and PDW, RDW is a function of the red FSL gain. When the red FSL gain is adjusted, the RDW values are checked. If they are outside the range, the RDW calibration factor and the previous red FSL gain is unapplied from the runs and the adjusted red FSL digital gain, from the previous step, is applied instead. For all runs, the updated RDW is calculated based on the current calibration factor and percentage of runs that are above or below the species-specific reference interval are determined. Next, fuzzy logic and gradient descent is used to calculate the smallest RDW calibration factor change that results in minimum reported values outside normal reference intervals.

The components of the automated calibration system and method, which are described above, may be realized by using a microprocessor, microcontroller or CPU 24, discrete electrical components or circuits, or software.

Automated diagnostic analyzers, such as hematology analyzers, can have their stability improved and bias reduced in accordance with the systems and methods described in the disclosure utilizing hematology fundamentals for red cell indices with species specific targets (for veterinary applications, in particular), quality control beads for setting digital gains, cross-species patient sample normalization, a gradient descent algorithm, and fuzzy logic. A simple PCV (packed cell volume) comparison with HCT can verify proper adjustments to the analyzer's settings and ensure accuracy with or without utilizing fixed cell controls or splitting samples with a reference laboratory. The systems and methods described herein are quite useful with veterinary hematology analyzers and in veterinary offices, where control fluid costs are prohibitive to their regular use, and many are based on human fixed cells requiring different algorithms than used with patient samples.

Using patient-based results to monitor and control system performance is effective since costly control runs do not have to performed. While a single patient-result will not provide ample power to make decisions and take actions regarding system performance, aggregated patient-based results provide increasing analytical power. As the number of samples for analysis increases, so does the analytical power. As the length of time and number of runs for analysis increases, so does the time before actions can be taken. Due to the desire to have high analytical power and quick response time, it is critical to balance the sample size with the required power for taking actions.

The fundamental assumption that must be met in order for the batches to be representative of the instrument response, and not patient results, is that samples included in a batch must be from a random population of patients. As long as the data set is random, samples are not repeated, and large groups (more than 30% of two consecutive batches worth of runs) of patient results with similar abnormal response conditions are not run in sequence, the statistics will be sufficient to generate batches that are representative of instrument response. These batches can then be used to adjust the system response for accuracy.

There are many benefits of utilizing batches to summarize patient samples into a control chart. Bull's logic provides a means to reduce the impact of single sample variations on batch results. Furthermore, utilizing this analysis for red cell parameters (RBC, HCT, HGB, MCV, MCH and MCHC) has additional benefits, since several parameters including MCV, MCH and MCHC have tight normal variations within species that can provide additional information with respect to result accuracy. Some concerns have been raised since the adjustment analysis references "targets" based on a central reference interval value for the particular parameter. These concerns are generally related to specialty practices running multiple sick patients, but this can be mitigated since there are few clinical conditions that drive significant variation in MCV, MCH, and MCHC for a population of patients. A practitioner can identify that the system is not functioning correctly when the population MCHC is biased above 37 or below 29; however, this analysis will utilize optimizing logic to find and correct biases before they are at this level of bias.

The described approach provides a means to ensure that the analysis system is functioning correctly, and provide feedback control to maintain accurate performance. Logic must be included to ensure that pre-analytical errors do not drive adjustments to the analyzer to compensate for bad preparation. For example, consistent pre-analytical errors causing in vitro hemolysis will result in high MCHC values, but the instrument should not be adjusted since it will cause accurate measurements to be biased due to the adjustment. Other pre-analytical concerns, such as the presence of significant lipemia, could also affect automated analysis. Logic can be put in place to block against some of these known conditions, but it is up to the practitioner to ensure that proper laboratory practices are employed to help ensure correct automated analyses.

Additional benefits are realized by ensuring performance with patient samples utilizing the described methods in conjunction with control fluids, since this provides another reference to add statistical power to the analysis. The application of this method of weighted moving averages analysis for other hematology parameters is possible. In addition, these methods may be optimized for chemistry analyzer performance and have potential value. The analytical power of the analysis is derived by the knowledge that mean values converge quickly, even in systems with large normal variation from the instrument and/or the sample population.

The systems and methods described herein make the adjustments, as required, to the calculations performed by the analyzer, in real time, without the need for the clinician to adjust the analyzer manually based on the clinician's interpretation of graphs and other data presented on a display of the analyzer, thereby minimizing or eliminating errors in the clinician's analysis or his possibly overcorrecting a perceived instrumentation bias.

In a first aspect A1, the present disclosure provides a processor-implemented method of calibrating a diagnostic analyzer, the method comprising receiving first diagnostic results from the diagnostic analyzer, the first diagnostic results being associated with the interrogation of polymer beads suspended in a fluid comprising dye by the diagnostic analyzer; determining whether the first diagnostic results exceed a configurable threshold from a first diagnostic target; adjusting, in a case where the first diagnostic results exceed the configurable threshold, one or more laser parameters; receiving a plurality of patient samples for interrogation by the diagnostic analyzer; normalizing the plurality of patient samples to account for cross-species differences; determining weighted averaged diagnostic results associated with the plurality of normalized patient samples interrogated by the diagnostic analyzer using the adjusted laser parameters; determining whether the weighted averaged diagnostic results fall outside of control chart rule limits; and, in a case where the weighted averaged diagnostic results fall outside of control chart rule limits, applying fuzzy logic and a gradient descent algorithm to the weighted averaged diagnostic results to obtain adjusted diagnostic results of the patient samples, and adjusting one or more settings of the diagnostic analyzer based at least in part on the adjusted diagnostic results.

In a second aspect A2, the present disclosure provides the method according to aspect A1, wherein the first diagnostic results are obtained by interrogating polymer beads, suspended in a fluidic dye, using the diagnostic analyzer.

In a third aspect A3, the present disclosure provides the method according to any one of aspects A1-A2, wherein the first diagnostic results are associated with a control run through the diagnostic analyzer.

In a fourth aspect A4, the present disclosure provides the method according to any one of aspects A1-A3, wherein the plurality of patient samples originate from a plurality of different species, and wherein the method further includes normalizing the plurality of patient samples to account for cross-species differences.

In a fifth aspect A5, the present disclosure provides the method according to any one of aspects A1-A4, wherein the permissible range is defined by control chart rules limits.

In a sixth aspect A6, the present disclosure provides the method according to any one of aspects A1-A5, wherein the one or more laser settings include a red laser forward scatter light (FSL) digital gain and a red laser extinction (EXT) digital gain.

In a seventh aspect A7, the present disclosure provides the method according to any one of aspects A1-A6, the determining of the weighted averaged diagnostic results further includes assembling the plurality of patient samples into a plurality of batch runs, each batch run containing an equal number of patient samples; determining the weighted average for a first batch run of the plurality of batch runs; calculating an absolute difference between each patient sample in a second batch run of the plurality of batch runs and the average for the first batch run; updating the weighted average for the first batch run using a sum of squared differences of the absolute differences for the second batch run to obtain a new weighted average for the first and second batch runs; and repeating the calculating and updating steps for each subsequent batch run of the plurality of batch runs.

In an eighth aspect A8, the present disclosure provides the method according to any one of aspects A1-A7, the determining of the one or more multiplying factors further includes setting fuzzy-logic derived confidence intervals for the one or more calibration factors; calculating a variance between a target value and the weighted averaged diagnostic results for the one or more parameters of the diagnostic analyzer; selecting a parameter of the one or more parameters for tuning, incrementally stepping the selected parameter towards the target value, and evaluating other parameters of the one or more parameters after stepping the selected parameter toward the target value; determining whether a stopping criterion is satisfied; and, in a case where the stopping criterion is satisfied, generating the one or more multiplying factors based on the tuned one or more parameters.

In a ninth aspect A9, the present disclosure provides the method according to aspect A8, wherein, in a case where the stopping criterion is not satisfied, the selecting step is repeated to perform further parameter tuning.

In a tenth aspect A10, the present disclosure provides the method according to any one of aspects A1-A9, wherein the diagnostic analyzer is a hematology analyzer and wherein the one or more parameters include red blood cell count (RBC), mean corpuscular volume (MCV), hemoglobin (HGB), platelet count (PLT), mean platelet volume (MPV), white blood cell count (WBC), hematocrit (HCT), mean corpuscular hemoglobin (MCH), mean corpuscular hemoglobin concentration (MCHC), platelet distribution width (PDW), and red blood cell distribution width (RDW).

In an eleventh aspect A11, the present disclosure provides a system for calibrating a diagnostic analyzer having one or more parameters, the system comprising at least one computer accessible-storage device configured to store instructions; and at least one processor communicatively connected to the at least one computer accessible storage device and configured to execute the instructions to: receive first diagnostic results from the diagnostic analyzer; determine whether the first diagnostic results exceed a predetermined threshold from a first diagnostic target; adjust, in a case where the first diagnostic results exceed the predetermined threshold, one or more laser settings for the diagnostic analyzer; receive a plurality of patient samples for interrogation by the diagnostic analyzer; determine weighted averaged diagnostic results associated with the plurality of patient samples interrogated by the diagnostic analyzer using the adjusted one or more laser settings and one or more calibration factors corresponding to the one or more parameters for the diagnostic analyzer; determine whether the weighted averaged diagnostic results fall outside of a permissible range; and, in a case where the weighted averaged diagnostic results fall outside of the permissible range: determine one or more multiplying factors for the one or more calibration factors that permit the weighted averaged diagnostic results to fall within the permissible range; and calibrate the diagnostic analyzer by adjusting the one or more calibration factors corresponding to the one or more parameters of the diagnostic analyzer based at least in part on the one or more multiplying factors.

In a twelfth aspect A12, the present disclosure provides the system according to aspect A11, wherein the first diagnostic results are obtained by interrogating polymer beads, suspended in a fluidic dye, using the diagnostic analyzer.

In a thirteenth aspect A13, the present disclosure provides the system according to any one of aspects A11-A12, wherein the first diagnostic results are associated with a control run through the diagnostic analyzer.

In a fourteenth aspect A14, the present disclosure provides the system according to any one of aspects A11-A13, wherein the plurality of patient samples originate from a plurality of different species, and wherein the at least one processor is further configured to execute the instructions to normalize the plurality of patient samples to account for cross-species differences.

In a fifteenth aspect A15, the present disclosure provides the system according to any one of aspects A11-A14, wherein the permissible range is defined by control chart rules limits.

In a sixteenth aspect A16, the present disclosure provides the system according to any one of aspects A11-A15, wherein the one or more laser settings include a red laser forward scatter light (FSL) digital gain and a red laser extinction (EXT) digital gain.

In a seventeenth aspect A17, the present disclosure provides the system according to any one of aspects A11-A16, wherein the at least one processor is further configured to execute the instructions to determine the weighted averaged diagnostic results by: assembling the plurality of patient samples into a plurality of batch runs, each batch run containing an equal number of patient samples; determining the weighted average for a first batch run of the plurality of batch runs; calculating an absolute difference between each patient sample in a second batch run of the plurality of batch runs and the average for the first batch run; updating the weighted average for the first batch run using a sum of squared differences of the absolute differences for the second batch run to obtain a new weighted average for the first and second batch runs; and repeating the calculating and updating steps for each subsequent batch run of the plurality of batch runs.

In an eighteenth aspect A18, the present disclosure provides the system according to any one of aspects A11-A17, wherein the at least one processor is further configured to execute the instructions to determine the one or more multiplying factors by: setting fuzzy-logic derived confidence intervals for the one or more calibration factors; calculating a variance between a target value and the weighted averaged diagnostic results for the one or more parameters of the diagnostic analyzer; selecting a parameter of the one or more parameters for tuning, incrementally stepping the selected parameter towards the target value, and evaluating other parameters of the one or more parameters after stepping the selected parameter toward the target value; determining whether a stopping criterion is satisfied; and, in a case where the stopping criterion is satisfied, generating the one or more multiplying factors based on the tuned one or more parameters.

In a nineteenth aspect A19, the present disclosure provides the system according to aspect A18, wherein, in a case where the stopping criterion is not satisfied, the selecting step is repeated to perform further parameter tuning.

In a twentieth aspect A20, the present disclosure provides the system according to any one of aspects A11-A19, wherein the diagnostic analyzer is a hematology analyzer and wherein the one or more parameters include red blood cell count (RBC), mean corpuscular volume (MCV), hemoglobin (HGB), platelet count (PLT), mean platelet volume (MPV), white blood cell count (WBC), hematocrit (HCT), mean corpuscular hemoglobin (MCH), mean corpuscular hemoglobin concentration (MCHC), platelet distribution width (PDW), and red blood cell distribution width (RDW).

In a twenty-first aspect A21, the present disclosure provides a non-transitory computer readable storage medium configured to store a program, executed by a computer, for a system for calibrating a diagnostic analyzer having one or more parameters, the program including instructions for: receiving first diagnostic results from the diagnostic analyzer; determining whether the first diagnostic results exceed a predetermined threshold from a first diagnostic target; adjusting, in a case where the first diagnostic results exceed the predetermined threshold, one or more laser settings for the diagnostic analyzer; receiving a plurality of patient samples for interrogation by the diagnostic analyzer; determining weighted averaged diagnostic results associated with the plurality of patient samples interrogated by the diagnostic analyzer using the adjusted one or more laser settings and one or more calibration factors corresponding to the one or more parameters for the diagnostic analyzer; determining whether the weighted averaged diagnostic results fall outside of a permissible range; and, in a case where the weighted averaged diagnostic results fall outside of the permissible range: determining one or more multiplying factors for the one or more calibration factors that permit the weighted averaged diagnostic results to fall within the permissible range; and calibrating the diagnostic analyzer by adjusting the one or more calibration factors corresponding to the one or more parameters of the diagnostic analyzer based at least in part on the one or more multiplying factors.

Although illustrative aspects of the present disclosure have been described herein with reference to the accompanying drawings, it is to be understood that the aspects of the disclosure are not limited to those precise aspects, and that various other changes and modifications may be effected therein by one skilled in the art without departing from the scope or spirit of the disclosure. Subsets or combinations of various aspects described above provide further aspects. These and other changes can be made to the disclosure and claims in light of the above-detailed description and still fall within the scope of the present disclosure and claims. In general, in the following claims, the terms used should not be construed to limit the claimed invention to the specific aspects disclosed in the specification. Accordingly, the claimed invention is not limited by the disclosure, but instead its scope is to be determined entirely by the following claims.

What is claimed is:

1. A processor-implemented method of calibrating a laser-based diagnostic analyzer having one or more parameters, the method comprising:

generating first diagnostic results by directing a laser beam through a plurality of polymer beads, suspended in a fluidic dye, using the laser-based diagnostic analyzer;

receiving the first diagnostic results from the laser-based diagnostic analyzer;

determining whether the first diagnostic results exceed a predetermined threshold from a first diagnostic target;

adjusting, in a case where the first diagnostic results exceed the predetermined threshold, one or more laser settings for the laser-based diagnostic analyzer;

receiving a plurality of patient samples for interrogation by the laser-based diagnostic analyzer;

generating second diagnostic results by directing the laser beam through the plurality of patient samples using the adjusted one or more laser settings for the laser-based diagnostic analyzer;

determining weighted averaged diagnostic results from the second diagnostic results and one or more calibration factors corresponding to the one or more parameters for the laser-based diagnostic analyzer;

determining whether the weighted averaged diagnostic results fall outside of a permissible range; and in a case where the weighted averaged diagnostic results fall outside of the permissible range:

determining one or more multiplying factors for the one or more calibration factors that permit the weighted averaged diagnostic results to fall within the permissible range; and calibrating the laser-based diagnostic analyzer by adjusting the one or more calibration factors corresponding to the one or more parameters of the laser-based diagnostic analyzer based at least in part on the one or more multiplying factors, thereby modifying an optical gain of the laser-based diagnostic analyzer to improve measurement accuracy of subsequent patient samples interrogated by the laser-based diagnostic analyzer.

2. The method according to claim 1, wherein the determining of the one or more multiplying factors further includes:

setting fuzzy-logic derived confidence intervals for the one or more calibration factors;

calculating a variance between a target value and the weighted averaged diagnostic results for the one or more parameters of the laser-based diagnostic analyzer;

selecting a parameter of the one or more parameters for tuning, incrementally stepping the selected parameter towards the target value, and evaluating other parameters of the one or more parameters after stepping the selected parameter toward the target value;

determining whether a stopping criterion is satisfied; and in a case where the stopping criterion is satisfied, generating the one or more multiplying factors based on the tuned one or more parameters.

3. The method according to claim 2, wherein, in a case where the stopping criterion is not satisfied, the selecting step is repeated to perform further parameter tuning.

4. The method according to claim 1, wherein the first diagnostic results are associated with a control run through the laser-based diagnostic analyzer.

5. The method according to claim 1, wherein the plurality of patient samples originate from a plurality of different species, and wherein the method further includes normalizing the plurality of patient samples to account for cross-species differences.

6. The method according to claim 1, wherein the permissible range is defined by control chart rules limits.

7. The method according to claim 1, wherein the one or more laser settings include a red laser forward scatter light (FSL) digital gain and a red laser extinction (EXT) digital gain.

8. The method according to claim 1, wherein the determining of the weighted averaged diagnostic results further includes:

assembling the plurality of patient samples into a plurality of batch runs, each batch run containing an equal number of patient samples;

determining the weighted average for a first batch run of the plurality of batch runs;

calculating an absolute difference between each patient sample in a second batch run of the plurality of batch runs and the average for the first batch run;

updating the weighted average for the first batch run using a sum of squared differences of the absolute differences for the second batch run to obtain a new weighted average for the first and second batch runs; and repeating the calculating and updating steps for each subsequent batch run of the plurality of batch runs.

9. The method according to claim 1, wherein the laser-based diagnostic analyzer is a hematology analyzer and wherein the one or more parameters include red blood cell count (RBC), mean corpuscular volume (MCV), hemoglobin (HGB), platelet count (PLT), mean platelet volume (MPV), white blood cell count (WBC), hematocrit (HCT), mean corpuscular hemoglobin (MCH), mean corpuscular hemoglobin concentration (MCHC), platelet distribution width (PDW), and red blood cell distribution width (RDW).

10. A system for calibrating a laser-based diagnostic analyzer having one or more parameters, the system comprising:

at least one computer accessible-storage device configured to store instructions; and at least one processor communicatively connected to the at least one computer accessible storage device and configured to execute the instructions to:

generate first diagnostic results by directing a laser beam through a plurality of polymer beads, suspended in a fluidic dye, using the laser-based diagnostic analyzer;

receive the first diagnostic results from the laser-based diagnostic analyzer;

determine whether the first diagnostic results exceed a predetermined threshold from a first diagnostic target;

adjust, in a case where the first diagnostic results exceed the predetermined threshold, one or more laser settings for the laser-based diagnostic analyzer;

receive a plurality of patient samples for interrogation by the laser-based diagnostic analyzer;

generate second diagnostic results by directing the laser beam through the plurality of patient samples using the adjusted one or more laser settings for the laser-based diagnostic analyzer;

determine weighted averaged diagnostic results from the second diagnostic results and one or more calibration factors corresponding to the one or more parameters for the laser-based diagnostic analyzer;

determine whether the weighted averaged diagnostic results fall outside of a permissible range; and in a case where the weighted averaged diagnostic results fall outside of the permissible range:

determine one or more multiplying factors for the one or more calibration factors that permit the weighted averaged diagnostic results to fall within the permissible range; and calibrate the laser-based diagnostic analyzer by adjusting the one or more calibration factors corresponding to the one or more parameters of the diagnostic analyzer based at least in part on the one or more multiplying factors, thereby modifying an optical gain of the laser-based diagnostic analyzer to improve measurement accuracy of subsequent patient samples interrogated by the laser-based diagnostic analyzer.

11. The system according to claim 10, wherein the at least one processor is further configured to execute the instructions to determine the one or more multiplying factors by:

setting fuzzy-logic derived confidence intervals for the one or more calibration factors;

calculating a variance between a target value and the weighted averaged diagnostic results for the one or more parameters of the laser-based diagnostic analyzer;

selecting a parameter of the one or more parameters for tuning, incrementally stepping the selected parameter towards the target value, and evaluating other parameters of the one or more parameters after stepping the selected parameter toward the target value;

determining whether a stopping criterion is satisfied; and in a case where the stopping criterion is satisfied, generating the one or more multiplying factors based on the tuned one or more parameters.

12. The system according to claim 11, wherein, in a case where the stopping criterion is not satisfied, the selecting step is repeated to perform further parameter tuning.

13. The system according to claim 10, wherein the first diagnostic results are associated with a control run through the laser-based diagnostic analyzer.

14. The system according to claim 10, wherein the plurality of patient samples originate from a plurality of different species, and wherein the at least one processor is further configured to execute the instructions to normalize the plurality of patient samples to account for cross-species differences.

15. The system according to claim 10, wherein the permissible range is defined by control chart rules limits.

16. The system according to claim 10, wherein the one or more laser settings include a red laser forward scatter light (FSL) digital gain and a red laser extinction (EXT) digital gain.

17. The system according to claim 10, wherein the at least one processor is further configured to execute the instructions to determine the weighted averaged diagnostic results by:

assembling the plurality of patient samples into a plurality of batch runs, each batch run containing an equal number of patient samples;

determining the weighted average for a first batch run of the plurality of batch runs;

calculating an absolute difference between each patient sample in a second batch run of the plurality of batch runs and the average for the first batch run;

updating the weighted average for the first batch run using a sum of squared differences of the absolute differences for the second batch run to obtain a new weighted average for the first and second batch runs; and repeating the calculating and updating steps for each subsequent batch run of the plurality of batch runs.

18. The system according to claim 10, wherein the laser-based diagnostic analyzer is a hematology analyzer and wherein the one or more parameters include red blood cell count (RBC), mean corpuscular volume (MCV), hemoglobin (HGB), platelet count (PLT), mean platelet volume (MPV), white blood cell count (WBC), hematocrit (HCT), mean corpuscular hemoglobin (MCH), mean corpuscular hemoglobin concentration (MCHC), platelet distribution width (PDW), and red blood cell distribution width (RDW).

19. A non-transitory computer readable storage medium configured to store a program, executed by a computer, for a system for calibrating a laser-based diagnostic analyzer having one or more parameters, the program including instructions for:

generating first diagnostic results by directing a laser beam through a plurality of polymer beads, suspended in a fluidic dye, using the laser-based diagnostic analyzer;

receiving the first diagnostic results from the laser-based diagnostic analyzer;

determining whether the first diagnostic results exceed a predetermined threshold from a first diagnostic target;

adjusting, in a case where the first diagnostic results exceed the predetermined threshold, one or more laser settings for the laser-based diagnostic analyzer;

receiving a plurality of patient samples for interrogation by the laser-based diagnostic analyzer;

generating second diagnostic results by directing the laser beam through the plurality of patient samples using the adjusted one or more laser settings for the laser-based diagnostic analyzer;

determining weighted averaged diagnostic results from the second diagnostic results and one or more calibration factors corresponding to the one or more parameters for the laser-based diagnostic analyzer;

determining whether the weighted averaged diagnostic results fall outside of a permissible range; and in a case where the weighted averaged diagnostic results fall outside of the permissible range:

determining one or more multiplying factors for the one or more calibration factors that permit the weighted averaged diagnostic results to fall within the permissible range; and calibrating the laser-based diagnostic analyzer by adjusting the one or more calibration factors corresponding to the one or more parameters of the laser-based diagnostic analyzer based at least in part on the one or more multiplying factors, thereby modifying an optical gain of the laser-based diagnostic analyzer to improve measurement accuracy of subsequent patient samples interrogated by the laser-based diagnostic analyzer.

* * * * *